United States Patent [19]

Tatsuki

[11] Patent Number: 4,552,149
[45] Date of Patent: Nov. 12, 1985

[54] HEAD COOLING IMPLEMENT

[75] Inventor: Tokuji Tatsuki, Osaka, Japan

[73] Assignee: Kabushiki Kaisha Dunlop Home Products, Kobe, Japan

[21] Appl. No.: 480,300

[22] Filed: Mar. 30, 1983

[30] Foreign Application Priority Data

Nov. 19, 1982 [JP] Japan .............. 57-176345[U]
Jan. 17, 1983 [JP] Japan ................ 58-5249[U]

[51] Int. Cl.⁴ ................................................ A61F 7/00
[52] U.S. Cl. ...................................... 128/402; 128/403
[58] Field of Search .................... 128/399, 402–403, 128/380

[56] References Cited

U.S. PATENT DOCUMENTS

| | | | |
|---|---|---|---|
| 3,463,161 | 8/1969 | Andrassy | 128/402 |
| 3,696,814 | 10/1972 | Umemoto | 128/402 X |
| 3,830,676 | 8/1974 | Elkins | 128/403 X |
| 4,061,898 | 12/1977 | Murray et al. | 128/380 X |
| 4,147,921 | 4/1979 | Walter et al. | 128/380 X |
| 4,190,054 | 2/1980 | Brennan | 128/402 |
| 4,354,496 | 10/1982 | Andersen | 128/399 X |
| 4,382,446 | 5/1983 | Trvelock et al. | 128/403 X |
| 4,425,916 | 1/1984 | Bowen | 128/402 X |
| 4,425,917 | 1/1984 | Kuznetz | 128/399 X |

FOREIGN PATENT DOCUMENTS 2948059 7/1981 Fed. Rep. of Germany ...... 128/402

Primary Examiner—Lee S. Cohen
Assistant Examiner—Angela D. Sykes
Attorney, Agent, or Firm—Armstrong, Nikaido, Marmelstein & Kubovcik

[57] ABSTRACT

A head cooling implement capable of covering the human skull like a cap for medical treatment. It comprises a main body consisting of a cooling piece for covering the top of the head and a plurality of cooling pieces radially arranged around the first-mentioned cooling piece for covering the front, sides and back of the head, each cooling piece being in the form of a sealed bag containing a coolant; a stretchable belt applied to the chin so as to bring the head top cooling piece of the main body into close contact with the top of the head; another stretchable belt adapted to bring the other cooling pieces of the main body into close contact with the skull at suitable places therearound; and a heat insulating cap to be put over the main body.

9 Claims, 8 Drawing Figures

HEAD COOLING IMPLEMENT

BACKGROUND OF THE INVENTION

The present invention relates to a head cooling implement capable of covering the skull of a patient like a cap for medical treatment and more particularly it relates to a head cooling implement which, by utilizing a cooling implement of the type comprising a bag formed of plastic sheet filled with an organic coolant and used by being cooled in the refrigerating chamber of a home refrigerator and applying it to the forehead or other affected part of a patient, is capable of being effectively applied to the head to cure side effects of a medicine.

Some of the recently developed medicines cause loss of the hair of patients to whom they are administered because of their side effects. However, there are many cases where continuous adminstration of such a medicine is desired because of its outstanding efficacy so long as the resulting loss of hair is not fatal. Thus, studies are being made to provide means for minimizing side effects, and there have recently been reported clinical cases indicating that side effects can be avoided by forcibly cooling the patient's head during administration of such a medicine.

Cooling implements commercially available today are limited to the pillow type and suspension type respectively represented by water pillows and ice bags, which are capable of cooling the skull only locally and which can be used only with a patient in a lying position. As for a new cooling implement, which is superseding the water pillows and ice bags, comprising a bag formed of plastic sheet and filled with an organic coolant or other chemical material, it is only of the headband type, so that even if capable of local cooling, it cannot bring about a perfect cooling effect with respect to side effects of medicines and moreover it has a drawback that it tends to come off the head owing to the patient shifting sleeping positions or doing other movements.

Accordingly, an object of the present invention is to provide a head cooling implement which is capable of more effectively cooling the entire skull, which during use, does not allow condensed waterdrops to drip and wet the hair or head skin, which does not tend to come off accidentally, and which is easy to put on.

SUMMARY OF THE INVENTION

The present invention is a head cooling implement comprising a main body consisting of a unit cooling piece polygonal or circular in shape for covering the top of the head and a plurality of unit cooling pieces radially arranged around the first-mentioned unit cooling piece for covering the front, sides and back of the head, a peripheral belt for bringing the plurality of unit cooling pieces of the main body, i.e., those unit cooling pieces which cover the front, sides and back of the head, into close contact with the periphery of the skull, a vertical belt applied to the chin to bring the head top cooling piece into close contact with the head top, and a heat insulating cap to be put over the main body to prevent the cold provided by the main body from escaping to the outside and to shut off the outside air.

The heat insulating cap principally intended to retain cold, in contrast with the main body principally intended to effect cooling, may be in the form of a cap having a chin strap or fastener-equipped belt attached thereto for fixing.

Further, in order to produce a stronger clamping action on the main body and hence on the skull, it is advantageous to provide the heat insulating cap with a size adjusting band adapted to engage a locking portion wherein the central portion is provided on the forehead region and the opposite end portions are provided on the opposite sides of the heat insulating cap.

The main body of the head cooling implement of the present invention is arranged so that when put on it is capable of covering the entire skull and so that it is mounted on the skull at all times. Further, prior to being mounted, the main body is powerfully cooled in a refrigerator. Thus, if the coolant held inside is of such a nature as will freeze as a whole upon cooling, it would give pain to the patient or other wearer and can hardly be closely contacted with the skull. Thus, it is preferable that the coolant used in the main body of the present invention be of such a nature as will not lose its suitable degree of softness as a whole even if cooled in a refrigerating chamber. A suitable material is a hydrophilic water-holding gel wrapped, in the form of a W/O type emulsion, in a synthetic high molecular material which exhibits little plastic deformation due to temperature, as disclosed in Japanese Patent Application published under No. 52-48895. Of course, any other known coolants that do not lose their suitable degree of softness upon powerful cooling may be used.

The coolant is sealed in a bag formed of a polyethylene, polyvinyl chloride or other soft material sheet to provide a unit cooling piece.

The main body of the present invention is capable of covering the entire skull when mounted and of conforming to the size of the skull of any wearer and being easily mounted, and preferably it is capable of being folded to reduce its volume to a minimum when it is cooled in a refrigerator. For this reason, the main body is composed of a plurality of unit cooling pieces, as previously described. If the main body is integrally constructed in the form of a cap, it would not be capable of closely contacting the surface of the skull or covering the entire surface of the skull owing to differences in the size of the skulls of wearers, thus resulting in a reduction in cooling effect.

Further, since the main body is powerfully cooled and then mounted because of its intended purpose, the moisture in the outside air condenses to form dewdrops on the outer surface of each unit cooling piece during use owing to differences in temperature between the outer surface and the outside air. To avoid unpleasant feeling caused by the dewdrops sticking to the hair or head skin or dripping to wet the wearer's clothes, each of the unit cooling pieces of the main body is inserted in a reticulate bag knitted or woven of a soft and water-repelling synthetic fiber. The mesh size of this reticulate bag is such as to prevent condensed waterdrops from passing therethrough but arrest them on the inner surface of the bag. Further, each unit cooling piece is designed to be capable of being put in and out of the reticulate bag to thereby make it possible to exchange unit cooling pieces when the function of the coolant has deteriorated or when cooling pieces have been damaged. Further, in order to make it possible to receive reticulate bags in smaller bulk in a refrigerator, they are designed so that they can be individually taken out of the reticulate bags and then received in separate condition. Thus, if each unit cooling piece is taken out of the reticulate bag and cooled alone, dew condensation on the surface of the reticulate bag can be avoided. For this reason, the reticulate bags are in the form of a pocket having an inlet-outlet port. Of course, the reticulate bags are separately constructed as the head top, front, sides and back portions corresponding to the respective unit cooling pieces, and the head front and subsequent reticulate bags are radially arranged around the head top reticulate bag and joined as by stitches to the latter.

The reticulate bags radially sewn around the head top portion have dimensional adjustability to some extent because of their stretchability so that they can fit to various sizes of skulls of patients. However, if necessary, stretchable fabric strips may be attached to the lateral edges of the reticulate bags disposed around the skull portion. Alternatively, for the purpose of interconnecting the lateral edges so as to completely surround the skull portion, a face-to-face engagement type fastener such as one sold under the name of Velcro (registered trademark) or another one sold under the name of Magic Fastener (registered trademark) may be attached to the front edges. Instead of such face-to-face engagement type fastener, it is possible to use other known locking elements such as slide fasteners, hooks, buttons and snaps.

In the main body of the present invention, the cooling piece for the forehead portion is designed so that its lower edge generally does not reach the eyebrows or at least the eyes of the wearer. Since cooling of the shallow head side (so-called temple) arteries upwardly branching from the carotid arteries is particularly effective to prevent loss of hair, it is preferable that the cooling pieces for the head sides be long enough to cover the lower portions of the cheeks. In this case, however, the head side cooling pieces would cover the earlobes, which can be easily frostbitten; thus, it would be thought to provide holes in the portions of the cooling pieces which contact the earlobes so as to clear the latter, but since the position and size of the earlobes differ from person to person, it seems better to apply some layers of gauze or absorbent cotton to the earlobes.

The main body of the present invention is put on the skull in close contact relation by using two stretchable belts.

Each of the two stretchable belts comprises sponge or felt, a stretchable fabric joined to the sponge or felt, and locking elements attached to the opposite ends of the belt, the sponge or felt surface serving as the inner surface. This arrangement ensures that they closely contact and engage the main body without any possibility of relative slippage, thus making it possible to prevent coming-off and slipping out of place. The locking elements are preferably face-to-face engagement type fasteners, but other locking elements such as clasps, hooks, and snaps may be used. One of the two stretchable belts is used to tie the cooling pieces disposed around the skull portion in a headband fashion extending from the forehead to the rear of the head, while the other extends from the front of the head to the chin to keep the head top cooling piece in close contact with the top of the head.

According to the head cooling implement of the present invention, after the main body has been mounted in place by means of the two stretchable belts, a heat insulating cap is put on the outer surface of the main body in order to increase the cooling effect. The heat insulating cap is in the form of an integral cap which is light in weight, soft and sturdy, allows little cold to escape, shuts off the outside air and covers the entire skull, the cap being prevented from falling off by means of a chin belt. Further, the outer periphery of the frusto-conical portion of the heat insulating cap has a portion of a size adjusting band joined thereto as by stitches. The interior size of the frusto-conical portion can be adjusted to the size of the head of a patient by adjusting the position of engagement where the locking element attached to the free end of the size adjusting band engages the locking element provided on the outer periphery of the frusto-conical portion of the heat insulating cap. The heat insulating cap has its inner surface formed of a plastic foamed sheet (about 1 mm thick) such as polyethylene, polystyrene or polyurethane and has on its outer surface a layer of plastic sheet composite material having an aluminum-deposited film, a layer having a reinforcing yarn reticulately arranged between the plastic sheet and aluminum-deposited film, or a layer of 100% nylon taffeta coated with a mixture of urethane and acrylic, the coated layer being colored blue or any other color desired, the inner surface of the nylon taffeta layer having superposed thereon an about 2-mm thick layer of plastic foamed sheet such as polyethylene, polystyrene or polyurethane, the inner surface of the foamed sheet layer having a covering fabric layer such as nylon applied thereto.

BRIEF DESCRIPTION OF THE DRAWINGS

These and other objects and features of this invention will become more apparent from the following description to be given with reference to the accompanying drawings, in which.

DESCRIPTION OF THE PREFERRED EMBODIMENTS

Figure 1:
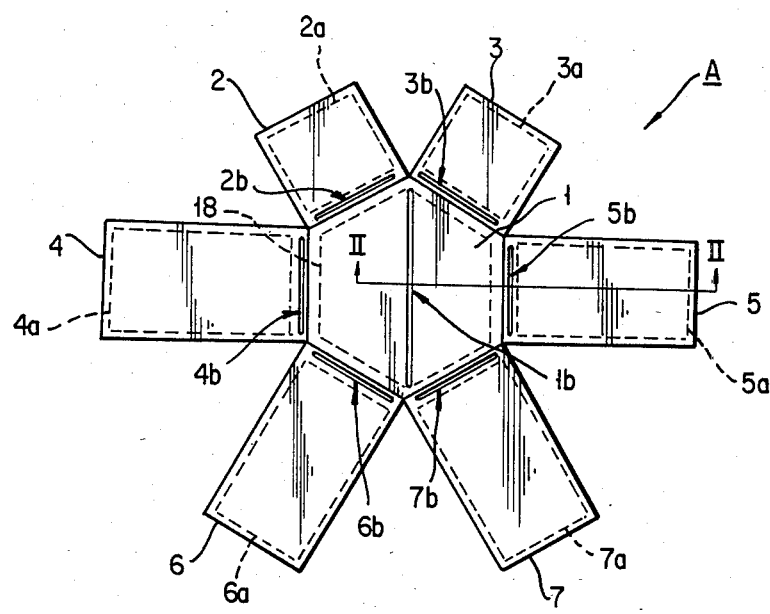
FIG. 1 is a developed view of the main body of a head cooling implement according to the invention.

Throughout the figures, like parts or portions are indicated by like reference numerals or characters.

Figure 2:
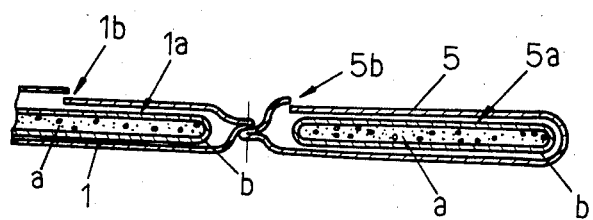
FIG. 2 is a sectional view taken along the line II—II of FIG. 1.

First, referring to FIG. 1, a main body is generally denoted by the character A, wherein 1 denotes a reticulate bag for the top of the head; 2 and 3 denote reticulate bags for the front of the head; 4 and 5 denote reticulate bags for the sides of the head; and 6 and 7 denote reticulate bags for the rear of the head, each reticulate bag having removably inserted therein through a inlet-outlet port 1b–7b a unit cooling piece 1a–7a in the form of a plastic film bag b having a coolant a sealed therein. The head top reticulate bag 1 is shown hexagonal in FIG. 1, but it may be of circular or any desired polygonal shape. The head front reticulate bags 2 and 3 are shorter in length than the head side reticulate bags 4 and 5 and head rear reticulate bags 6 and 7 and are long enough to terminate just above the eyes. The head top reticulate bag 1 and the reticulate bags 2–7 disposed around the same are joined together, as by stitches, in the manner shown in FIG. 2. The inlet-outlet ports 1b–7b formed in the reticulate bags 1–7 may be formed at any desired position, but in consideration of the ease with which the unit cooling pieces 1a–7a are put in and out and for the purpose of preventing their falling off, the position shown in FIG. 1 is preferable. It seems preferable that the edges of the inlet-outlet ports 1b–7b overlap each other to some extent, as shown in FIG. 2. The unit cooling pieces 1a–7a to be inserted in the reticulate bags 1–7 are of the same or approximately the same shape as their respective associated reticulated bags, and it suffices for the purpose that those cooling pieces which are disposed around the periphery are approximately rectangular, but in some cases they may be fan-shaped or barrel-shaped.

Figure 3:
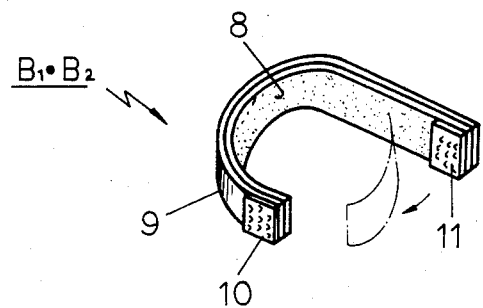
FIG. 3 is a perspective view of a stretchable belt used to improve contact of the main body with the skull.

FIG. 3 is a perspective view of a stretchable belt B1, B2 used in the present invention, comprising a sponge or felt layer 8 forming the inner side, a suitable stretchable fabric layer 9 forming the outer side, the two layers being joined together to have stretchability as a whole, and female and male locking elements 10 and 11 in the form of a face-to-face engagement type fastener attached to the opposite ends of the belt.

Figure 4:
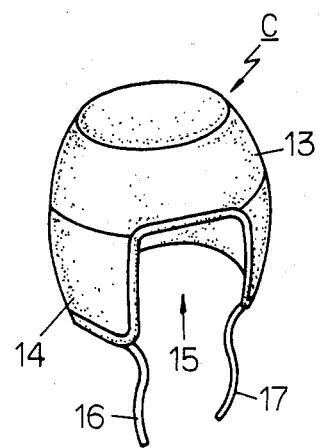
FIG. 4 is a perspective view of a heat insulating cap.

FIG. 4 is a perspective view of a heat insulating cap C used in the present invention, which is in the form of a helmet type cap wherein the region above the lower edge of the forehead portion is substantially a frusto-conical portion 13, while the region therebelow is constricted at the rear lower end thereof to form a skirt portion 14 adapted to cover the cheeks and the rear of the head, and a face portion 15 is cut out, with chin straps 16 and 17 attached to the lower ends of the opposite sides of the face portion 15.

Figure 5:
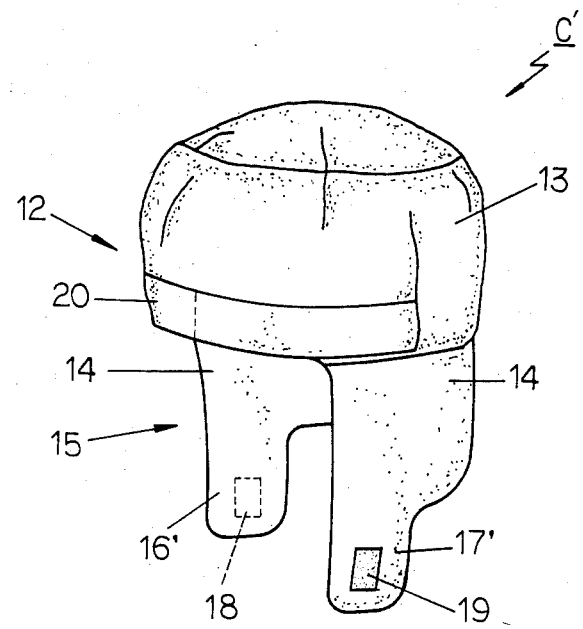
FIG. 5 is a perspective view of a somewhat modified heat insulating cap.
Figure 6:
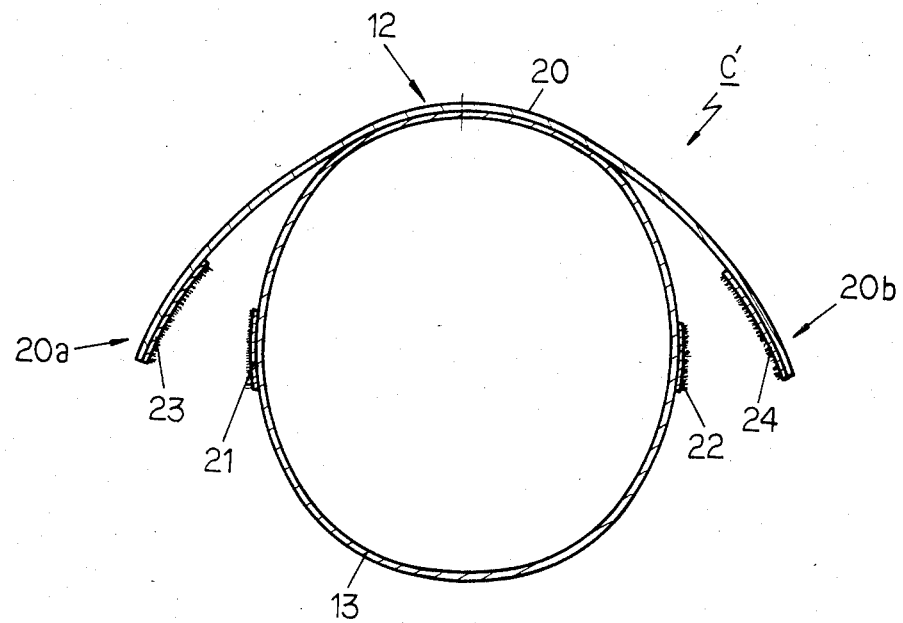
FIG. 6 is a cross-sectional view of the heat insulating cap of FIG. 5.
Figure 7:
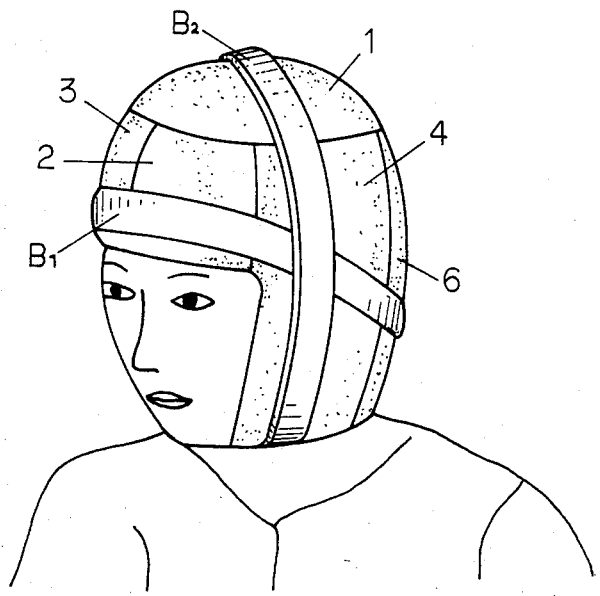
FIG. 7 is a schematic view showing how the main body and the stretchable belt are mounted.

FIGS. 5 and 6 show a somewhat modified heat insulating cap C′, wherein the lower portions of the opposite sides of the face portion 15, check belts 16′ and 17′ having female and male locking elements 18 and 19 in the form of face-to-face engagement type fasteners attached to the lower ends thereof, respectively, are integrally formed in the lower regions of the skirt portions 14, 14. The numeral 20 denotes a size adjusting band attached to the forehead portion 12 of the frusto-conical portion 13 so as to adjust the inner diameter of the frusto-conical portion 13 of the heat insulating cap C′. The size adjusting band 20 is joined, as by stitches, at its middle to the forehead portion 12 of the frusto-conical portion 13 of the heat insulating cap, as shown in FIG. 6. Further, its opposite ends 20a and 20b have attached thereto somewhat longer face-to-face engagement type fasteners 23 and 24 adapted to engage the face-to-face engagement type fasteners 21 and 22 attached to the opposite sides of the frusto-conical portion 13 of the heat insulating cap. Thus, the diameter of the frusto-conical portion 13 of the heat insulating cap can be adjusted by adjusting the position of engagement where the face-to-face engagement type fasteners 23 and 24 attached to the opposite ends of the dimensional adjustment band 20 engage the face-to-face engagement type fasteners 21 and 22 attached to the opposite sides of the frusto-conical portion 13 of the heat insulating cap so as to constrict the forehead portion 12 of the heat insulating cap C′.

In addition, the position where the size adjusting band 20 is joined to the heat insulating cap C′ is not limited to the forehead portion 12 of the heat insulating cap C′, as in this embodiment, and it may be the sides or rear of the head of the heat insulating cap C′.

As for the components of the heat insulating cap, as described above, the inner side is a foamed sheet and the outer side is a suitable covering (having air-impermeability) which is colored. The cap is soft as a whole.

Figure 8:
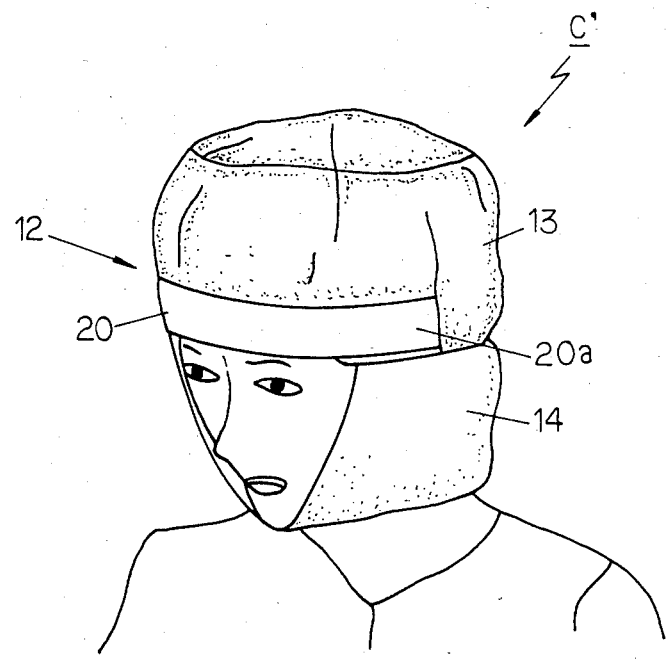
FIG. 8 is a schematic view showing the heat insulating cap in its mounted position.

The way of putting on the head cooling implement of the present invention will now be described. The main body A, which has been precooled, is mounted on the head of the wearer so that it assumes a suitable position, and then its periphery is clampled by the peripheral stretchable belt B1 in a headband fashion, as shown in FIG. 6. At this time, gauze or absorbent cotton is applied, in layers of suitable thickness, to the earlobes. In order to fit to the size and length of the skull and the hair style of the wearer, the main body is tucked up and down or drawn back and forth or right and left so as to cover the entire skull. The head top portion is clamped against the chin by the vertical stretchable belt B2. As a result, the head top cooling piece is brought into close contact with the top of the head and the peripheral cooling pieces are brought into close contact with the periphery of the skull and fixed. The heat insulating cap is then put on. In the case of the cap C shown in FIG. 4, the chin straps 15 and 16 are tightened to complete the operation. Tightening the chin straps 15 and 16 causes the heat insulating cap C to bring the cooling pieces into closer contact with the entire skull, thus preventing cold from escaping, and shutting off the outside air to increase the cooling effect. In the case of the cap C′, the heat insulating cap C′ is put over the main body A, as shown in FIG. 8, and the position of engagement where the face-to-face engagement type fasteners 23 and 24 attached to the ends of the size adjusting band 20 engage the face-to-face engagement type fasteners 21 and 22 attached to the opposite sides of the frusto-conical portion 13 of the heat insulating cap is adjusted to constrict the forehead portion 13 of the heat insulating cap C′, thereby bringing the frusto-conical portion 13 of the heat insulating cap C′ into close contact with the main body A. Finally, the locking element 18 attached to one chin belt 16′ of the heat insulating cap C′ is brought into engagement with the locking element 19 attached to the other chin belt 17′, thereby bringing the heat insulating cap C′ into closer contact with the main body A and concurrently preventing the heat insulating cap C′ from slipping off the head; thus, the mounting of the head cooling implement is completed. If the heat insulating cap C′ is brought into close contact with the main body A in this manner by tightening the size adjusting band 20 and chin belts 16′ and 17′, it is possible to bring the cooling pieces into closer contact with the entire skull, thus preventing cold from escaping, and shutting off the outside air so as to increase the cooling effect. Further, the frusto-conical portion 13 of the heat insulating cap C′ can be positively contacted with the skull of the wearer irrespective of its size by the action of the size adjusting band 20 joined to the outer periphery thereof. Thus, the heat insulating cap C′ is prevented from slipping out of position when the wearer turns over in bed or walks around.

While the above embodiments have been described as being used to avoid side effects of medicines, the present invention can, of course, be utilized to cool the head of a patient suffering from a fever in general.

As has been described so far, since the head cooling implement of the present invention has a main body comprising a head top portion and a peripheral portion radially connected thereto, the implement is capable of absorbing differences in the size of the skulls of wearers and fitting to any person. Further, since the unit cooling pieces have a suitable degree of softness even when powerfully cooled, they satisfactorily conform to the shape of the skull. Further, since the unit cooling pieces are inserted in reticulate bags, there is no possibility of an unpleasant feeling being caused by condensed waterdrops passing through the meshes under the action of their surface tension and sticking to the hair or head skin or dripping down to wet the clothes. Further, the main body can be folded to reduce its volume to a minimum and then put in a refrigerator. The main body is closely contacted with and clamped against the entire skull of the wearer by the two peripheral and vertical stretchable belts, improving the cooling action and preventing it from falling off the head and particularly preventing its shifting movement. The heat insulating cap allows the cooling action of the cooling pieces to be retained for a long period of time, and allows the unit cooling pieces to be brought into closer contact with the skull by the clamping of the chin straps. Further, it is in the form of a cap of suitable color, neatly concealing the main body inside it, not causing a sense of incompatibility, preventing the cooling pieces inside from slipping out of position when the wearer turns over in bed, and enabling the wearer to walk around with the implement on.

As many apparently widely different embodiments of this invention may be made without departing from the spirit and scope thereof, it is to be understood that the invention is not limited to the specific embodiments described herein and shown in the drawings except as defined in the appended claims.

What is claimed is:

1. A head cooling implement comrising:
   a main body consisting of a first cooling piece for covering the top of the head and a plurality of other cooling pieces radially arranged around said first cooling piece and positioned for covering the front, sides and back of the head, each said cooling piece comprising a sealed bag containing a coolant;
   a first stretchable belt means adapted to be applied over the top of the head and under the chin so as to bring said head top cooling piece of said main body into close contact with the top of the head;
   a second stretchable belt means adapted to bring said other cooling pieces of said main body into close contact with the skull at suitable places therearound; and
   a heat insulating cap which covers said main body.

2. A head cooling implement as set forth in claim 1, wherein said head top cooling piece is circular and said other cooling pieces are attached to the periphery thereof.

3. A head cooling implement as set forth in claim 1, wherein said head top cooling piece is polygonal and each of said other cooling pieces is attached to one of the sides thereof along one edge of said other cooling piece.

4. A head cooling implement as set forth in claim 1, wherein each cooling piece of said main body is wrapped in a reticulate bag of knitted woven soft and water-repelling synthetic fiber.

5. A head cooling implement as set forth in claim 4, wherein said cooling pieces constituting said main body are separate from each other, and said reticulate bags consist of a portion wrapping the head top cooling piece and a plurality of portions radially arranged therearound, said portions individually receiving said cooling pieces.

6. A heading cooling implement as set forth in claim 1, wherein said cooling pieces constituting said main body are in the form of sealed bags formed of a soft sheet, each containing a coolant such as a synthetic high molecular material, which develops little plastic deformation due to a temperature change without losing a suitable degree of softness.

7. A head cooling implement as set forth in claim 1, wherein said heat insulating cap includes a frusto-conical portion and a size adjusting band having a portion thereof joined to said frusto-conical portion, said adjusting band having a free end which engages with engaging means provided on said frusto-conical portion.

8. A head cooling implement as set forth in claim 1, wherein said heat insulating cap has a chin strap.

9. A head cooling implement as set forth in claim 8, wherein said chin strap is in the form of a belt with a fastener.

* * * * *